United States Patent [19]

Kitagawa et al.

[11] Patent Number: 5,574,054
[45] Date of Patent: Nov. 12, 1996

[54] QUATERNARY AMMONIUM SALTS AND USE THEREOF AS MEDICINE

[75] Inventors: Osamu Kitagawa; Katsuyuki Ishii; Seiichi Niwa; Sigeru Ueki; Masao Seiki, all of Konanmachi, Japan

[73] Assignee: Zeria Pharmaceutical Co., Ltd., Tokyo, Japan

[21] Appl. No.: 325,338

[22] PCT Filed: May 10, 1993

[86] PCT No.: PCT/JP93/00607

§ 371 Date: Jan. 12, 1995

§ 102(e) Date: Jan. 12, 1995

[87] PCT Pub. No.: WO93/23360

PCT Pub. Date: Nov. 25, 1993

[30] Foreign Application Priority Data

May 12, 1992 [JP] Japan .................................. 4-145062

[51] Int. Cl.[6] .................. C07D 277/28; C07D 307/52; C07D 333/22; C07C 211/63
[52] U.S. Cl. .................. 514/365; 548/205; 549/495; 549/75; 564/288; 564/237; 564/45; 564/47; 564/23; 564/27; 514/438; 514/471; 514/580; 514/595; 514/643
[58] Field of Search ............ 548/205; 514/365, 514/438, 471, 580, 595, 643; 549/495, 75; 564/288, 237, 45, 47, 23, 27

[56] References Cited

U.S. PATENT DOCUMENTS

| | | | |
|---|---|---|---|
| 4,128,658 | 12/1978 | Price et al. | 424/285 |
| 4,169,855 | 10/1979 | Price et al. | 260/583 EE |
| 4,255,440 | 3/1981 | Price et al. | 424/274 |
| 4,279,819 | 7/1981 | Price et al. | 260/326.5 S |
| 4,375,547 | 5/1983 | Pioch | 548/205 |
| 4,382,090 | 5/1983 | Pioch | 424/270 |
| 4,760,075 | 7/1988 | Pioch | 514/365 |
| 4,904,792 | 2/1990 | Pioch | 548/205 |
| 4,923,882 | 5/1990 | Hirai et al. | 514/326 |
| 5,017,608 | 5/1991 | Aschwanden et al. | 514/538 |
| 5,075,301 | 12/1991 | Sasho et al. | 514/211 |
| 5,300,493 | 4/1994 | Romeo et al. | 514/54 |

FOREIGN PATENT DOCUMENTS 0049618 4/1982 European Pat. Off. .

OTHER PUBLICATIONS

Journal of Organic Chemistry, vol. 51, No. 5, pp. 730–732, Mar. 7, 1986, Jacob Herzig, et al., "Studies in Ranitidine Chemistry: An Unusual O→N Methyl Migration".
Knadler et al., Drug Metab. and Dis., 14(2), 175–182, (1986).
Sano et al., Xenobiotica, 21(10), 1257–1264, (1991).
Sano et al., Arzneim.–Forsch./Drug Res., 41(II), Nr. 9, 961–964, (1991).
Spec. Publ.—R. Soc. Chem. 42, pp. 45–57, J. Bradshaw, et al., "Aminoalkylfurans as H2–Receptor Antagonists" (1982).

Primary Examiner—Johann Richter
Assistant Examiner—Laura R. Cross
Attorney, Agent, or Firm—Oblon, Spivak, McClelland, Maier & Neustadt, P.C.

[57] ABSTRACT

Novel quaternary ammonium salts having utility in the medical field for treating gastrointestinal disorders.

4 Claims, No Drawings

QUATERNARY AMMONIUM SALTS AND USE THEREOF AS MEDICINE

This application is a 371 of PCT/JP93/00607 filed May 10, 1993 and published as WO93/23360 Nov. 25, 1993.

1. Technical Field

The present invention relates to novel quaternary ammonium salts and use of the salts as medicines.

2. Background Art

Conventionally, trimebutine maleate has been primarily used as a gastroprokinetic agent.

Trimebutine maleate has wide utility due to its dual activities of promoting and suppressing the gastric contractions. However, it is not necessarily satisfactory in that relatively high dose, i.e., 300 mg per day is required, and that adverse side effects are involved.

Therefore, studies have been conducted in search for gastroprokinetic agents which can replace trimebutine maleate (Japanese Patent Application Laid-open (kokai) No. 163074/1991).

However, the results have not necessarily been successful in providing gastroprokinetics. Accordingly, development of drugs which possess much stronger activity in enhancement of gastrointestinal motility has still been desired.

DISCLOSURE OF THE INVENTION

Accordingly, the present invention provides novel quaternary ammonium salts represented by the following formula (I):

$$R^2-\overset{R^1}{\underset{A}{N^+}}(CH_2)_l-X-(CH_2)_m-Y-(CH_2)_n-\underset{H}{N}-Z-\underset{H}{N}-R^3 \; Q^-$$

[wherein $R^1$ and $R^2$ represent lower alkyl groups which may be the same or different from each other; $R^3$ represents hydrogen, lower alkyl, phenyl, benzyl, or $-COOR^4$ (wherein $R^4$ represents lower alkyl); A represents lower alkyl, lower alkenyl, lower alkynyl, $-(CH_2)_p-COOR^5$ (wherein $R^5$ represents hydrogen or lower alkyl, and p represents an integer of from 1 to 5)

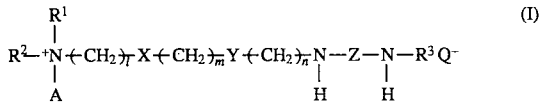

wherein $R^6$ represents hydrogen, hydroxyl, nitro, lower alkyl, $-COOR^5$, or $-SO_3R^5$); $Q^{31}$ represents a counter anion of quaternary ammonium salt; X represents

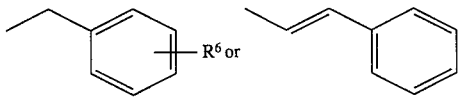

Y represents methylene, oxygen or sulfur; Z represents

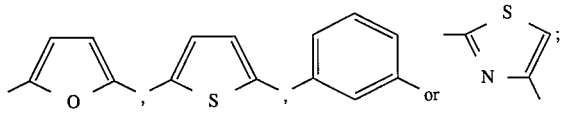

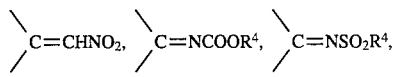

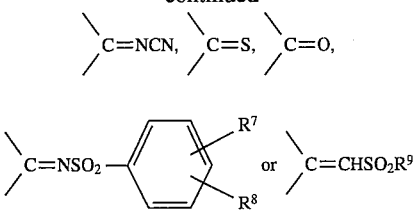

(wherein $R^7$ and $R^8$ are the same or different from each other and independently represent hydrogen, halogen, nitro, lower alkyl or lower alkoxyl, and $R^9$ represents lower alkyl or phenyl); l and m represent each an integer of 1 or 2; and n represents an integer of from 1 to 3], and use of the salts as medicines.

Since the compounds according to the present invention have an activity of accelerating the gastrointestinal contractions, i.e., they improve the gastrointestinal motility remarkably, as well as high safety, they have utility in the medical field of treating the gastrointestinal disorders and the like.

BEST MODE FOR CARRYING OUT THE INVENTION

In the present invention, the term "lower alkyl" encompasses alkyl groups having 1 to 5 carbon atoms, examples of which include methyl, ethyl, propyl, isopropyl, butyl, isobutyl, sec-butyl, tert-butyl, pentyl, isopentyl, neopentyl, tert-pentyl and the like.

The term "lower alkenyl" encompasses alkenyl groups having 2 to 5 carbon atoms, which include vinyl, allyl, butenyl, 3-methyl-2-butenyl and the like.

The term "lower alkynyl" encompasses alkynyl groups having 2 to 5 carbon atoms, which include ethynyl, propargyl and the like.

Examples of the counter anion of quaternary ammonium salt include fluorine ion, chlorine ion, bromine ion, iodine ion, $HSO_4^-$, $ClO_3^-$, $NO_3^-$, cyanide ion, $HSO_3^-$ ion, $IO_3^-$ ion, $HCO_2^-$, $CH_3CO_2^-$, $OH^-$, phenolate ion, methanesulfonate ion, toluenesulfonate ion and the like.

The compound (I) of the present invention is prepared, for example, by the following reaction scheme:

Method A

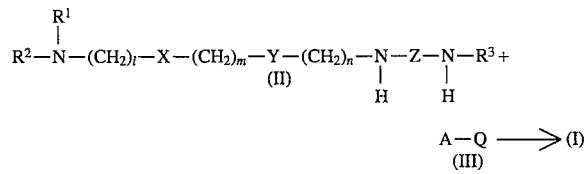

(wherein $R^1$, $R^2$, $R^3$, A, Q, X, Y, Z, l, m and n have the same meaning as defined hereinbefore).

That is, compound (I) is obtained by reacting compound (II) which is obtainable by applying a known method (Japanese Patent Application Laid-open (kokai) No. 40956/1983; Japanese Patent Application Laid-open (kokai) No. 91980/1982; R. Soc. Chem., 42, Regul. Biol. Mech., 45–47, 1982) with compound (III).

The above reaction is preferably carried out in an inert solvent such as methanol, ethanol, dichloromethane, chloroform, ethyl acetate, dimethylformamide, dimethylsulfoxide and water, in a temperature range of 0° C. to a reflux temperature. It is preferred that the compounds (II) and (III) be used in an equimolar amount, or one be used in a slightly larger amount than the other. The reaction time is desirably varied according to the progress and condition of the reaction.

Alternatively, the compound (I) of the present invention may be prepared according to the following reaction scheme:

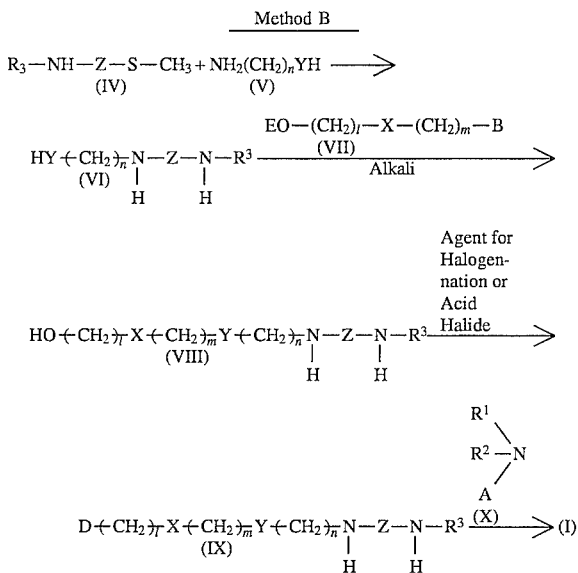

(wherein $R^1$, $R^2$, $R^3$, A, X, Y, Z, l, m and n have the same meaning as defined hereinbefore, E represents a protective group for an alcohol such as benzoyl and acetyl, B represents a halogen atom, and D represents a halogen atom or an acid residue).

That is, compound (I) of the present invention is obtained by reacting a halogen compound or an ester compound (IX) with an amine compound (X).

The reaction for synthesizing the compound (VI) is preferably carried out in an anhydrous organic solvent, especially under stream of an inert gas such as argon. The reaction temperature is preferably within the range of 0° C. to a boiling point, and more preferably, at room temperature. The reaction for synthesizing the compound (VIII) is carried out in the presence of an alkali such as KOH, NaOH and the like, during which the protective group is removed. In the reaction for synthesizing the compound (IX), an organic base may be added if desired. Preferable examples of the agent for halogenation include phosphorus oxychloride. Preferable examples of the acid halide include methanesulfonic acid chloride and toluenesulfonic acid chloride.

The compound (I) of the present invention has excellent activity in stimulation of gastrointestinal motility as will be described later in this specification.

The compound (I) of the present invention can be formulated into a drug preparation for oral or parenteral administration after blended with pharmaceutically acceptable adjuvants. In the manufacture of oral-route preparations, the compound of the invention is blended with suitable additives, for example, vehicles such as lactose, mannitol, corn starch and crystalline cellulose; binders such as cellulose derivatives, gum arabic and gelatin; disintegrators such as carboxymethylcellulose calcium; and lubricants such as talc and magnesium stearate, and formed into tablets, powders, granules, capsules and the like. The obtained solid preparations may further be coated using coating bases such as hydroxypropylmethylcellulose phthalate, hydroxypropylmethylcellulose acetate succinate, cellulose acetate phthalate and methacrylate copolymers and formed into enteric preparations. In the manufacture of parenteral preparations, the compounds of the invention may be combined, for example, with water, ethanol, glycerol or surfactants which are commonly used in this technical field and prepared into injection preparations; or combined with suppository bases to prepare suppositories.

The amounts of administration of the compound (1) of the present invention vary depending on age, body weight, symptom of the disease, goal of the treatment, manner of administration, period of administration, etc. Generally, in the case of oral administration, the compound is administered in amounts of 1–2000 mg/day, preferably 10–300 mg/day, as divided in 1 to 3 times a day.

Action

Acceleration of Gastrointestinal Motility:

The test was performed according to the method of Itoh et al. (Am. J. Dig. Dis. 22, 117–124, 1977).

In detail, laparotomy was made to male dogs (body weight: 9–10 kg) under anesthesia with Nembutal (30 mg/kg, i.v.). Force transducers (F-121S, manufactured by Star Medical Co.) were implanted so that the contraction of circular muscle could be monitored on serosa of the gastric body, gastric antrum (about 3 cm proximal to the pylorus), duodenum and jejunum. In addition, a silicone tube was inserted from the right external carotid artery, and the tube was indwelled in the superior vena cava. The transducers and the silicone tube were subcutaneously exteriorized out of the body.

The dog was submitted to the test with consciousness and without restraint after about 3 weeks from the operation.

The contractile signals from each transducer were amplified with an amplifier (RTA-1200; manufactured by Nihon Kohden Co.), and recorded with a recording apparatus and a computer. The test compounds were dissolved in saline and intravenously administered (0.5 ml/kg) to the dogs through a silicone tube about 10 minutes after the termination of phase III contractions of interdigestive migrating contractions (IMC) in the antrum.

Evaluation Method:

Contractile signals from the antrum amplified in analog voltage were converted to digital signals, which were integrated to calculate the motor activity. The quantity of work which allows to sustain the maximum contraction in phase III contractions of IMC for 6 seconds was considered as 1 unit, and the motor index (units/30 min) in the period of 30 minutes after the administration of the test compound was obtained. The thus calculated motor index was compared with the motor index obtained after saline was administered.

The results are shown in Table 1.

TABLE 1

| Test Compounds | Dose (mg/Kg) | Motor Index (units/30min) |
|---|---|---|
| Example 1 | 5 | 7.5 |
| Example 6 | 5 | 6.1 |
| Example 9 | 5 | 7.1 |
| Example 11 | 5 | 10.9 |
| Example 12 | 5 | 9.4 |
| Example 14 | 5 | 6.6 |
| Example 16 | 5 | 4.3 |
| Saline | — | 0.1 |

Toxicity Test:

Groups of 4–5 week old ICR mice, each group consisting of 6 mice, were provided for the test. The compounds obtained in the Examples were respectively suspended in 5% gum arabic and each suspension was orally administered to the mice at a dose of 1000 mg/kg. The mice were observed for 1 week. None of the mice died in any dosage groups.

EXAMPLES

The present invention will hereinafter be described in more detail by way of examples, which however should not be construed as limiting the invention thereto.

Example 1

Trimethyl=[4-[[[2-[(1-methylamino-2-nitroethenyl)-amino]ethyl]thio]methyl]-2-thiazolyl]methylammonium= iodide

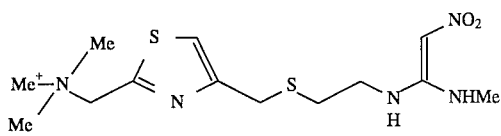

N-[2-[[[2-[dimethylamino)methyl-4-thiazolyl]methyl]thio]ethyl]-N'-methyl-2-nitro-1,1-ethenediamine (5 g) was dissolved in chloroform (50 ml). To this mixture, methyl iodide (2.19 g) was added dropwise while cooling on ice. After stirring for 24 hours at 0° C., the solvent was distilled off. The residue was purified by alumina column chromatography (chloroform—water) to obtain 6.8 g of the title compound. IR (KBr) cm⁻: 1380 MS (m/z): 346 (M-I)⁺

NMR (DMSO-$d_6$) δ: 2.55–2.90(5H, m), 3.15(9H, s), 3.33–3.47(2H, m), 3.97(2H, s), 4.94(2H, s), 6.50(1H, brd), 7.25(1H, brs), 7.80(1H, s), 9.99 (1H, brd)

Examples 2 to 18

The procedure of Example 1 was repeated, using starting materials which were suitably selected to obtain the compounds of Examples 2 to 18.

Example 2

Trimethyl=[4-[[[2-[(1-methylamino-2-nitrotheny-l)amino]ethyl]thio]methyl]-2-thiazolyl]methylammonium= bromide

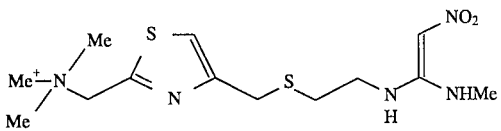

IR (nujol) cm⁻¹: 1380 MS (m/z): 346(M-Br)⁺
NMR (DMSO-$d_6$) δ: 2.60–2.95(5H, m), 3.19(9H, s), 3.30–3.50(2H, m), 3.98(2H, s), 5.01(2H, s), 6.50(1H, brd), 7.36(1H, brs), 7.83(1H, s), 9.99(1H, brd)

Example 3

Ethyl=dimethyl=[4-[[[2-[(1-methylamino-2-nitroetheny-l)amino]ethyl]thio]methyl]-2-thiazolyl]methylammonium= bromide

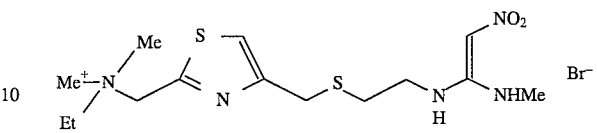

IR (KBr) cm³¹ ¹: 1385 MS (m/z): 360(M-Br)⁺
NMR (DMSO-$d_6$) δ: 1.34(3H, t), 2.60–3.00(5H, m), 3.08(6H, s), 3.30–3.50(2H, m) 3.44(2H, q) 3.97(2H, s) 4.94(2H, s), 6.50(1H, brd), 7.31(1H, brs), 7.8(1H, s), 9.95(1H, brd)

Example 4

Benzyl=dimethyl=[4-[[[2-[(1-methylamino-2-nitroethe-nyl)amino]ethyl]thio]methyl]-2-thiazolyl]methylammo-nium=chloride

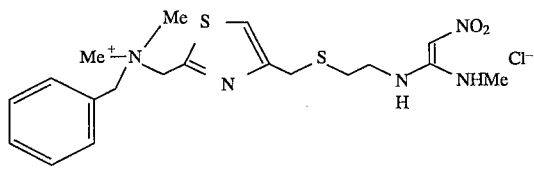

IR (KSr) cm⁻¹: 1385 MS (m/z): 422(M-Cl)⁺
NMR (DMSO-$d_6$) δ: 2.60–2.95(5H, m), 3.04(6H, s), 3.30–3.60(2H, m), 4.01(2H, s), 4.75(2H, s), 4.99(2H, s), 6.50(1H, brd), 7.40–7.70(6H, m), 7.86(1H, s), 9.95(1H, brd)

Example 5

Dimethyl=4-nitrobenzyl=[4-[[[2-[(1-methylamino-2-ni-troethenyl)amino]ethyl]thio]methyl]-2-thiazolyl]-methy-lammonium=bromide IR (KBr) cm$^{-1}$: 1385 MS (m/z): 467(M-Br)$^+$ NMR (MeOH-d$_4$) δ: 2.75–2.95(5H, m), 3.18(6H,s), 3.48(2H, t), 4.02(2H,s), 4.89(2H, s), 4.98(2H, s), 6.70(1H, brs), 7.73(1H, s), 8.01(2H, d), 8.38(2H, d)

Example 6

Dimethyl=propargyl=[4-[[[2-[(1-ethylamino-2-nitroethenyl)amino]ethyl]thio]methyl]-2-thiazolyl]methylammonium=bromide

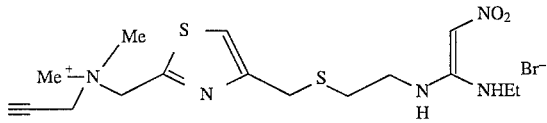

IR (KBr)cm$^{-1}$: 2120, 1390 MS (m/z): 384(M-Br)$^+$

NMR (DMSO-d$_6$) δ: 1.09(3H, brs), 2.69(2H, brs), 3.19(6H, s), 3.05–3.55(4H, m), 3.94(2H, s), 4.08(1H, s), 4.51(2H, s), 5.03(2H, s), 6.48(1H, s), 7.31(1H, brs), 7.81(1H, s), 10.00(1H, brd)

Example 7

Dimethyl=propargyl=[4-[[[2-[(3-methylureido)ethyl]thio]methyl]-2-thiazolyl]methylammonium=bromide

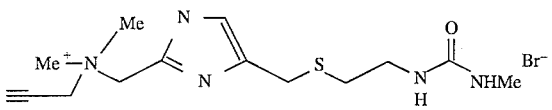

IR (KBr)cm$^{-1}$: 2125, 1690 MS (m/z): 327(M-Br)$^+$

NMR (DMSO-d$_6$) δ: 2.50–2.56(5H, m), 3.12–3.40(2H, m), 3.2(6H, s), 3.92(2H, s), 4.12(1H, brs), 4.50(2H, d), 5.02(2H, s), 5.86(1H, brs), 6.06(1H, brs), 7.81(1H, s)

Example 8

Trimethyl=[2-[[[2-[(1-methylamino-2-nitroethenyl)amino]ethyl]thio]methyl]-5-furanyl]methylammonium=iodide

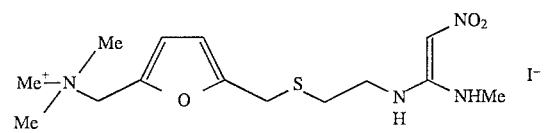

IR (KBr) cm$^{-1}$: 1385 MS (m/z): 329(M-I)$^+$

NMR (DMSO-d$_6$) δ: 2.60–2.90(5H, m), 3.04(9H, s), 3.30–3.48(2H, m), 3.89(2H, s), 4.61(2H, s), 6.46(1H, d), 6.48(1H, brs), 6.76(1H, d), 7.22(1H, brs), 9.98(1H, brd)

Example 9

Dimethyl=propargyl=[2-[[[2-[(1-methylamino)-2-nitroethenyl)amino]ethyl]thio]methyl]-5-furanyl]methylammonium=bromide

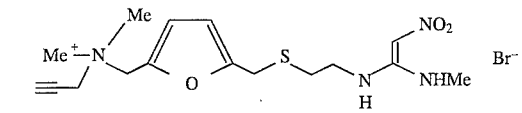

IR (KBr)cm$^{-1}$: 2125, 1385 MS (m/z): 353(M-Br)$^+$

NMR (DMSO-d6) δ: 2.62–2.93(5H, m), 3.07(6H, s), 3.30–3.50(2H, m), 3.89(2H, s), 4.09(1H, t), 4.35(2H, d), 4.68(2H, s), 6.47(1H, d), 6.50(1H, brs), 6.79(1H, d), 7.32(1H, brd), 9.99(1H, brd)

Example 10

Benzyl=dimethyl=[2-[[[2-[(1-methylamino-2-nitroethenyl)amino]ethyl]thio]methyl]-5-furanyl]methylammonium=bromide

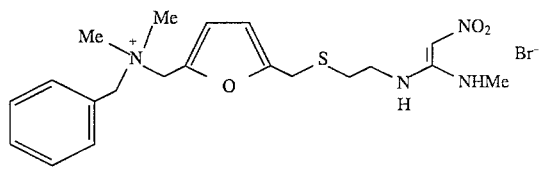

IR (KBr) cm$^{-1}$: 1385 MS (m/z): 405(M-Br)$^+$

NMR (DMSO-$_6$) δ: 2.61–2.95(5H, m), 2.97(6H, s), 3.31–3.61(2H, m), 3.94(2H, s), 4.73(2H, s), 4.78(2H, s), 6.46(1H, brs), 6.48(1H, d), 6.86(1H, d), 7.42(1H, brs), 7.50–7.58(3H, m), 7.64–7.71(2H, m), 10.01(1H, brd)

Example 11

Allyl=dimethyl=[4-[[[2-[(1-methylamino-2-nitroethenyl)amino]ethyl]thio]methyl]-2-thiazolyl]-methylammonium=bromide

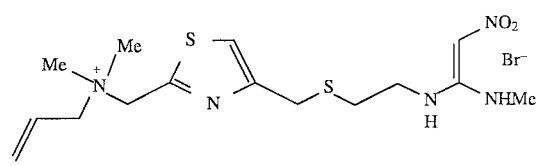

IR (KBr) cm$^{-1}$: 1380 MS (m/z): 372(M-Br)$^+$

NMR (DMSO-$_6$) δ: 2.55–3.00(5H, m), 3.09(6H, s), 3.33–3.55(2H, m), 3.98(2H, s), 4.10(2H, d), 4.95(2H, s), 5.62–5.73(2H, m), 6.02–6.23(1H, m), 6.46(1H, brd), 7.30(1H, brs), 7.81(1H, s), 9.99(1H, brd)

Example 12

Dimethyl=propargyl-[4-[[[2-[(1-methylamino-2-nitroethenyl)amino]ethyl]thio]methyl]-2-thiazolyl]-methylammonium=bromide

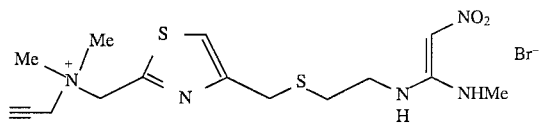

IR (KBr) cm$^{-1}$: 2120, 1380 MS (m/z): 370(M-Br)$^+$

NMR (DMSO-d$_6$) δ: 2.53–2.92(5H, m), 3.19(6H, s), 3.39–3.60(2H, m), 3.97(2H, s), 4.12(1H, t), 4.47(2H, d), 5.00(2H, s), 6.49(1H, brd), 7.30(1H, brs), 7.82(1H, s), 9.99(1H, brd)

Example 13

Dimethyl=3-methyl-2-butenyl=[4-[[[2-[(1-methylamino-2-nitroethenyl)amino]ethyl]thio]methyl-2-thiazolyl]methylammonium=bromide

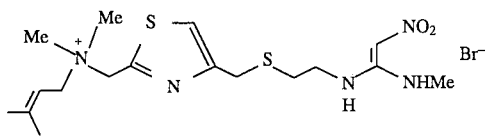

IR (KBr) cm$^{-1}$: 1380 MS (m/z): 400(M-Br)$^+$

NMR (DMSO-d$_6$) δ: 1.78(3H, s), 1.85(3H, s), 2.60–2.90(5H, m), 3.03(6H, s), 3.30–3.50(2H, m), 3.98(2H, s), 4.06(2H, d), 4.92(2H, s), 5.50(1H, t), 6.44(1H, brs), 7.38(1H, brs), 7.37(1H, brs), 9.98(1H, brd)

Example 14

Benzyl=dimethyl=[4-[[[2-[(1-methylamino-2-nitroethenyl)amino]ethyl]thio]methyl]-2-thiazolyl]methylammonium=bromide

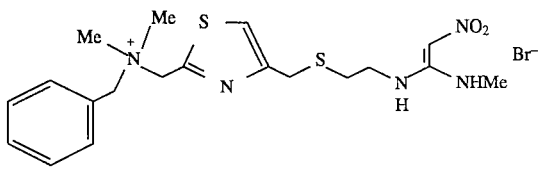

IR (KBr) cm$^{-1}$: 1380 MS (m/z): 422(M-Br)$^+$

NMR (DMSO-d$_6$) δ: 2.60–2.90(5H, m), 3.06(6H, s), 3.37–3.55(2H, m), 4.01(2H, s), 4.78(2H, s), 5.01(2H, s), 6.48(1H, brd), 7.37(1H, brs), 7.49–7.57(3H, m), 7.67–7.70(2H, m), 7.86(1H, s), 9.95(1H, brd)

Example 15

Dimethyl=propargyl=[3-[[[2-[(1-methylamino-2-nitroethenyl)amino]ethyl]thio]methyl]benzylammonium=bromide

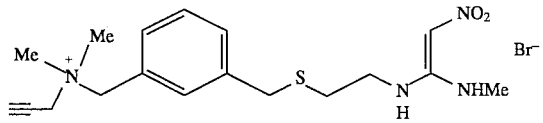

IR (KBr) cm$^{-1}$: 2120, 1385 MS (m/z): 363(M-Br)$^+$

NMR (DMSO-d$_6$) δ: 2.50–2.90(5H, m), 3.05(6H, s), 3.25–3.45(2H, m), 3.86(2H, s), 4.15(1H, t), 4.30(2H, d), 4.59(2H, s), 6.46(1H, brs), 7.27(1H, brs), 7.44–7.54(4H, m), 9.97(1H, brd)

Example 16

Dimethyl=propargyl=[2-[[[2-[(1-methylamino-2-nitroethenyl)amino]ethyl]thio]methyl]-5-thienyl]methylammonium=bromide

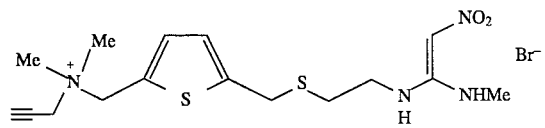

IR (KBr) cm$^{-1}$: 2110, 1380 MS (m/z): 369(M-Br)$^+$

NMR (DMSO-d$_6$) δ: 2.60–2.95(5H, m), 3.11(6H, s), 3.30–3.50(2H, m), 4.12(2H, s), 4.15(1H, s), 4.36(2H, s), 4.85(2H, s), 6.46(1H, s), 7.12(1H, d), 7.28(1H, d), 7.35(1H, brs), 10.00(1H, brd)

Example 17

Cinnamyl=dimethyl=[4-[[[2-[(1-methylamino-2-nitroethenyl)amino]ethyl]thio]methyl]-2-thiazolyl]methylammonium=bromide

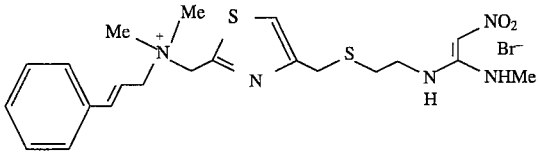

IR (KBr) cm$^{-1}$: 1380 MS (m/z): 448(M-Br)$^+$

NMR (DMSO-d$_6$) δ: 2.57–2.85(5H, m), 3.13(6H, s), 3.20–3.50(2H, m), 4.00(2H, s), 4.24(2H, d), 4.98(2H, s), 6.44(1H, brs), 6.56(1H, dr), 6.95(1H, d), 7.25(1H, brs), 7.36–7.63(5H, m), 7.82(1H, s), 9.97(1H, brd)

Example 18

Trimethyl=[4-[[[2-[(1-methylamino-2-nitroethenyl)amino]ethyl]thio]methyl]-2-thiazolyl]methylammonium=p-toluenesulfonato

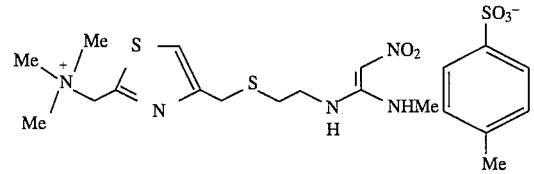

IR (KBr) cm$^{-1}$: 1390 MS (m/z): 346(M-C$_7$H$_7$SO$_3$)$^+$

NMR (DMSO-d$_6$) δ: 2.29(3H, s), 2.60–2.90(5H, m), 3.16(9H, s), 3.42(2H, m), 3.96(2H, s), 4.95(2H, s), 6.50(1H, brd), 7.13(2H, d), 7.32(1H, brs), 7.51(2H, d), 7.80(1H, s), 10.00(1H, brd)

Example 19

Trimethyl=[4-[[[2-[(1-methylamino-2-nitroethenyl)amino]ethyl]thio]methyl]-2-thiazolyl]methylammonium=chloride

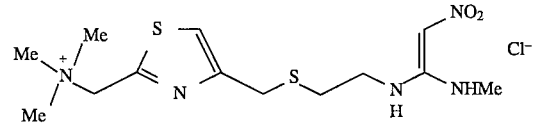

Method A:

The compound (20 g) obtained in Example 1 was allowed to pass through an anion exchange resin column (IRA-900, Cl-type), and eluted with purified water. The solvent in the eluted fraction was distilled off under reduced pressure to obtain 14.6 g of the target compound. IR (nujol) cm$^{-1}$: 1380 MS (m/z): 346(M-Cl)$^+$ NMR (DMSO-d$_6$) δ: 2.51–2.91(5H, m), 3.21(9H, s), 3.30–3.50(2H, m), 3.99(2H, s), 5.07(2H, s), 6.50(1H, brd), 7.80(1H, brs), 7.86(1H, s), 9.99(1H, brd)

Method B:

(1) N-[2-[[(2-hydroxymethyl-4-thiazolyl)methyl]thio]ethyl]-N'-methyl-2-nitro-1,1-ethenediamine Under stream of argon, 1-methylamino-1-methylthio-2-nitroethene (16.6 g) was dissolved in absolute methanol (300 ml), to which 2-aminoethanethiol (8.64 g) was added. The obtained mixture was stirred for 30 minutes at room temperature, and the solvent was distilled off under reduced pressure. The residue was dissolved in an aqueous KOH solution (1.1N, 200 ml). This aqueous solution was added dropwise to a mixture of 2-benzoyloxymethyl-4-chloromethylthiazol (25.0 g) and methanol (250 g) while cooling on ice. The resulting mixture was stirred for 1 hour in an ice bath, and further for 4 hours at room temperature. Subsequently, the solvent was distilled off under reduced pressure. The residue was purified by alumina column chromatography (chloroform—methanol), recrystallized from methanol-ethyl acetate to obtain 12.4 g of the title compound. m.p. 131.3°–132.3° C. IR (KBr) cm$^{-1}$: 3165, 1625, 1560, 1375 MS (m/z): 305(MH$^+$)

NMR (DMSO-d$_6$) δ: 2.70(3H, brd), 2.83(2H, brd), 3.36(2H, brd), 3.84(2H, s), 4.69(2H, d), 6.01(1H, t), 6.44(1H, brd), 7.22(1H, brd), 7.39(1H, s), 10.04(1H, brd)

(2) N-[2-[(2-chloromethyl-4-thiazolyl)methyl]-thio]ethyl]-N'-methyl-2-nitro-1,1-ethenediamine N-[2-[[(2-hydroxymethyl-4-thiazolyl)methyl]thio]ethyl]-N'-methyl-2-nitro-1,1-ethenediamine (1 g) obtained in (1) above was added to phosphorus oxychloride (15 ml), and the mixture was stirred for 21 hours at room temperature. The reaction mixture was concentrated under reduced pressure. The residue was combined with ice-water, and then extracted with ethyl acetate. The extract was washed with saturated NaCl solution, followed by drying over magnesium sulfate. The solvent was distilled off under reduced pressure, and the residue was purified by silica gel column chromatography (chloroform—methanol) to obtain 420 mg of the title compound. IR (CHCl$_3$) cm$^{-1}$: 1610, 1570, 1385 MS (m/z): 323(MH$^+$)

NMR (DMSO-d$_6$) δ: 2.75(2H, t), 2.78(3H, d), 3.38(2H, q), 3.88(2H, s), 5.00(2H, s), 6.43(1H, s), 7.24(1H, brd), 7.51(1H, s), 10.05(1H, brd)

(3) Trimethyl=[4-[[[2-[(1-methylamino-2-nitroethenyl)amino]ethyl]thio]methyl]-2-thiazolyl]methylammonium=chloride N-[2-[[(2-chloromethyl-4-thiazolyl)methyl]thio]ethyl]-N'-methyl-2-nitro-1,1-ethenediamine (394 mg) obtained in (2) above was dissolved in methanol (10 ml), into which trimethylamine was blown while cooling the mixture on ice. The resulting mixture was stirred overnight at room temperature, and the solvent was distilled off under reduced pressure. The residue was purified by alumina column chromatography (chloroform—methanol) to obtain 250 mg of the title compound. IR (nujol) cm$^{-1}$: 1380 MS (m/z): 346(M-Cl)$^+$ NMR (DMSO-d$_6$) δ: 2.51–2.91(5H, m), 3.21(9H, s), 3.30–3.50(2H, m), 3.99(2H, s), 5.07(2H, s), 6.50(1H, brd), 7.80(1H, brs), 7.86(1H, s), 9.99(1H, brd)

Formulation Example 1:

| Compound of Example 1 | 20 g |
| Lactose | 315 g |
| Corn starch | 125 g |
| Crystalline cellulose | 25 g |

The above ingredients were blended into a uniform mixture, to which 200 ml of 7.5% aqueous hydroxypropylcellulose solution was added, and then passed an extruder equipped with a screen of 0.5 mm in diameter to prepare granules. Immediately thereafter, the granules were rounded with a marumerizer and dried to obtain a granule preparation.

Formulation Example 2:

| Compound of Example 11 | 20 g |
| Lactose | 100 g |
| Corn starch | 36 g |
| Crystalline cellulose | 30 g |
| Carboxymethylcellulose calcium | 10 g |
| Magnesium stearate | 4 g |

The above ingredients were blended into a uniform mixture, and prepared into tablets each weighing 200 mg with a single-shot tableting machine equipped with a pestle having a diameter of 7.5 mm.

Formulation Example 3:

| Compound of Example 12 | 100 mg |
| Sodium acetate | 2 mg |
| Acetic acid (for adjusting pH to 5.8) | suitable amount |
| Purified water | suitable amount |
| Total: | 10 ml/vial |

The above formulation was prepared into an injection preparation by a method known per se.

Industrial Applicability

Since the compounds according to the present invention have activity of accelerating the gastrointestinal contraction or of improving the gastrointestinal motility remarkably as well as high safety, they have utility in the medical field of treating gastrointestinal disorders, etc.

We claim:

1. A quaternary ammonium salt represented by the following formula (I):

$$R^2-{}^+\!N\!\!+\!CH_2\!\!\!+\!_l\!X\!\!+\!CH_2\!\!\!+\!_m\!Y\!\!+\!CH_2\!\!\!+\!_n\!N\!-\!Z\!-\!N\!-\!R^3\,Q^-$$
(with $R^1$ above N, A below first N, H below middle N, H below last N)   (I)

wherein $R^1$ and $R^2$ represent lower alkyl groups which may be the same or different from each other; $R^3$ represents hydrogen, lower alkyl, phenyl, benzyl, or —COOR$^4$, wherein $R^4$ represents lower alkyl; A represents lower alkyl, lower alkenyl, lower alkynyl, —(CH$_2$)$_p$—COOR$^5$, wherein $R^5$ represents hydrogen or lower alkyl, and p represents an integer of from 1 to 5,

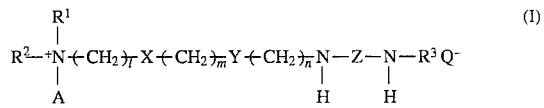

wherein $R^6$ represents hydrogen, hydroxyl, nitro, lower alkyl, —COOR$^5$, or —SO$_3$R$^5$; Q$^-$ represents a counter anion of quaternary ammonium salt; X represents

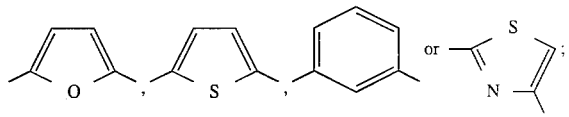

Y represents methylene, oxygen or sulfur; Z represents

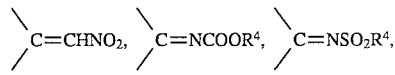

-continued

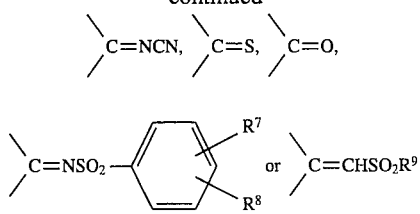

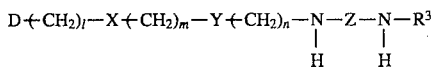

wherein $R^7$ and $R^8$ are the same or different from each other and independently represent hydrogen, halogen, nitro, lower alkyl or lower alkoxyl, and $R^9$ represents lower alkyl or phenyl; l and m each represent an integer of 1 or 2; and n represents an integer of from 1 to 3.

2. A medicinal composition comprising the quaternary ammonium salt of claim 1 and a pharmaceutically acceptable adjuvant.

3. A method of treating gastrointestinal disorders in a patient which comprises treating said patient with an effective amount of the quaternary ammonium salt of claim 1.

4. A compound represented by the following formula (IX):

$$D \!-\!\!(CH_2)_l\!-\!X\!-\!\!(CH_2)_m\!-\!Y\!-\!\!(CH_2)_n\!-\!\underset{H}{N}\!-\!Z\!-\!\underset{H}{N}\!-\!R^3$$

wherein $R^3$ represents hydrogen, lower alkyl, phenyl, benzyl, or —COOR$^6$, wherein $R^6$ represents lower alkyl; D represents halogen or an active ester residue; X represents

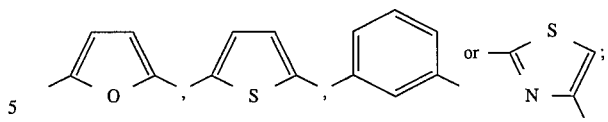

Y represents methylene, oxygen or sulfur; Z represents

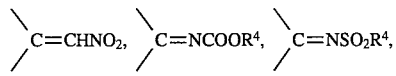

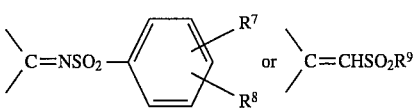

wherein $R^7$ and $R^8$ are the same or different from each other and independently represent hydrogen, halogen, nitro, lower alkyl or lower alkoxyl, and $R^9$ represents lower alkyl or phenyl; l and m each represent an integer of 1 or 2; and n represents an integer of 1 to 3.

* * * * *